United States Patent
Park et al.

(10) Patent No.: US 12,087,421 B2
(45) Date of Patent: Sep. 10, 2024

(54) AI-BASED PRODUCT SURFACE INSPECTING APPARATUS AND METHOD

(71) Applicant: INTER X CO., LTD., Ulsan (KR)

(72) Inventors: Jung Ywn Park, Ulsan (KR); Ha Il Jung, Ulsan (KR); Jeong Hyun Park, Ulsan (KR)

(73) Assignee: INTER X CO., LTD., Ulsan (KR)

( * ) Notice: Subject to any disclaimer, the term of this patent is extended or adjusted under 35 U.S.C. 154(b) by 0 days.

(21) Appl. No.: 18/541,004

(22) Filed: Dec. 15, 2023

(65) Prior Publication Data

US 2024/0112781 A1 Apr. 4, 2024

Related U.S. Application Data

(63) Continuation of application No. 18/149,762, filed on Jan. 4, 2023, which is a continuation of application No. PCT/KR2022/018411, filed on Nov. 21, 2022.

(30) Foreign Application Priority Data

Dec. 16, 2021 (KR) ........................ 10-2021-0180195

(51) Int. Cl.
*G06Q 20/16* (2012.01)
*G01N 21/88* (2006.01)
(Continued)

(52) U.S. Cl.
CPC ......... *G16H 20/10* (2018.01); *G01N 21/8851* (2013.01); *G06Q 20/16* (2013.01);
(Continued)

(58) Field of Classification Search
CPC ... G01N 21/8851; G16H 380/00; G06Q 20/16
See application file for complete search history.

(56) References Cited

U.S. PATENT DOCUMENTS

2019/0197679 A1 * 6/2019 Fang ...................... G06N 3/084
2020/0334446 A1 * 10/2020 Fang ................... G06V 20/698

FOREIGN PATENT DOCUMENTS

KR 20090018978 * 3/2009 ............ G06T 7/001
KR 10-2010-0088421 8/2010
(Continued)

OTHER PUBLICATIONS

'Validation of Building Power Consumption Prediction Accuracy According to Frozen Number of Layers based on Transfer Learning', J. Korean Solar Energy Society, 2020, vol. 40, No. 6, pp. 151-160.

*Primary Examiner* — Myron Wyche
(74) *Attorney, Agent, or Firm* — NKL Law; Byungwong Park

(57) ABSTRACT

Disclosed are a product surface inspecting apparatus and method which detect a defect on products having different feature using a previously trained artificial neural network. A product surface inspecting apparatus according to an exemplary embodiment includes a sensor unit which photographs a product to generate image data and measures at least one of a color, a saturation, a brightness, a transparency, and a reflectance of the product; and a detection unit which detects a defect on a product by inputting the image data to a convolutional neural network trained to detect a defect on a product surface, the number of convolution layers of the convolutional neural network may be determined based on at least one of the color, the saturation, the brightness, the transparency, and the reflectance of the product.

13 Claims, 4 Drawing Sheets

(51) Int. Cl.
    *G16H 20/10*          (2018.01)
    *G16H 80/00*          (2018.01)
    *G16H 10/60*          (2018.01)

(52) U.S. Cl.
    CPC ..... *G16H 80/00* (2018.01); *G01N 2021/8854* (2013.01); *G06V 2201/06* (2022.01); *G16H 10/60* (2018.01)

(56) References Cited

FOREIGN PATENT DOCUMENTS

| | | | | |
|---|---|---|---|---|
| KR | 101863196 | * | 6/2018 | ............ G06T 7/001 |
| KR | 10-2021-0040853 | | 4/2021 | |
| KR | 102254773 | * | 5/2021 | ............ G06Q 50/08 |
| KR | 10-2260169 | | 6/2021 | |
| KR | 10-2263716 | | 6/2021 | |
| KR | 10-2274389 | | 7/2021 | |
| KR | 10-2021-0115356 | | 9/2021 | |
| KR | 10-2296511 | | 9/2021 | |
| WO | 2020031984 | | 2/2020 | |

* cited by examiner

AI-BASED PRODUCT SURFACE INSPECTING APPARATUS AND METHOD

CROSS-REFERENCE TO RELATED APPLICATIONS

This application is a continuation of U.S. Non-Provisional patent application Ser. No. 18/149,762, filed on Jan. 4, 2023, which is a continuation of International Application No. PCT/KR2022/018411, filed on Nov. 21, 2022, which claims priority from Korean Patent Application No. 10-2021-0180195, filed on Dec. 16, 2021, the disclosures of the aforementioned applications are hereby incorporated by reference in their entireties.

TECHNICAL FIELD

The present disclosure relates to a technique for inspecting a surface of a product, and more particularly, to a product surface inspecting apparatus and a method which detect a defect on products having different features using a previously trained artificial neural network.

BACKGROUND

Recently, studies on a method for detecting a defect of a product by means of image analysis using an artificial neural network are being conducted. However, the artificial neural network for analyzing an image requires a large amount of training data regardless of a learning method. However, in many manufacturing environments, it is difficult to secure training data enough to train an artificial neural network.

Further, the performance of the artificial neural network varies depending on the training data so that sophisticated training data is required. When the training data which is classified according to incorrect standards at the manufacturing site is used, the performance of the artificial neural network may be significantly degraded.

Accordingly, it is necessary to develop an apparatus which detects a defect of the product having a feature different from the training data in various manufacturing sites using an artificial neural network which learns various defect types appearing on a product surface using precisely designed training data in advance.

SUMMARY

An object is to provide a product surface inspecting apparatus and a method which detect a defect on products having different features using a previously trained artificial neural network. According to an aspect, a product surface inspecting apparatus includes: a sensor unit which photographs a product to generate image data and measures at least one of a color, a saturation, a brightness, a transparency, and a reflectance of the product; and a detection unit which detects a defect on a product by inputting the image data to a convolutional neural network trained to detect a defect on a product surface, the number of convolution layers of the convolutional neural network may be determined based on at least one of the color, the saturation, the brightness, the transparency, and the reflectance of the product.

The convolutional neural network may perform the learning by receiving a predetermined size of training image data for a first defect type to divide the training image data into grids having a predetermined size.

The training image data is configured by a three-channel image obtained by dividing an image for the same product with respect to the RGB and a size of the training data is 448×448, and a size of the grid is 7×7.

The convolutional neural network may perform the learning as many as the number obtained by dividing a size of one training image data by a size of the grid.

The convolutional neural network may learn N defect types.

The number of convolution layers of the convolutional neural network may be determined based on a similarity between at least one of the color, the saturation, the brightness, the transparency, and the reflectance of the product used as the training data of the convolutional neural network and at least one of the color, the saturation, the brightness, the transparency, and the reflectance of the product.

The number of convolution layers of the convolutional neural network may be increased in inverse proportion to the similarity.

The product surface inspecting apparatus may further include: a preprocessor which converts the image data based on at least one of the color, the saturation, the brightness, the transparency, and the reflectance of the product to input the converted data to the detection unit.

The preprocessor may perform auto cropping to extract a shape of the product from the image data to extract at least one feature of a brightness and a shadow of the product based on a shape of the automatically cropped product.

The preprocessor may convert at least one of the color, the saturation, and the brightness of the image data with respect to at least one of the color, the saturation, and the brightness of the product used as the training data of the convolutional neural network.

The preprocessor may determine a frequency of an image sharpening filter based on a transparency of the product and convert the image data by applying the image sharpening filter to the image data.

The detection unit may detect a position of a defect, a size of the defect, and a type of defect on the product and if a predetermined number or more of defects of the same position, same size, and same type consistently occur, it may be determined that the defect is not a defect.

The detection unit may display a bounding box on the image data based on the position of the defect and the size of the defect present in the product and output image data displayed with the bounding box and the type of the defect.

According to an aspect, a product surface inspecting method may include: generating image data by photographing a product; measuring at least one of a color, a saturation, a brightness, a transparency, and a reflectance of a product; and detecting a defect on a product by inputting the image data to a convolutional neural network trained to detect a defect on a product surface, the number of convolution layers of the convolutional neural network may be determined based on at least one of color, saturation, brightness, transparency, and reflectance of the product.

The defect on products having different features in various manufacturing sites may be effectively and quickly detected with a small amount of image data using a previously trained artificial neural network specified for product surface inspection.

DESCRIPTION OF EXEMPLARY EMBODIMENTS

Hereinafter, exemplary embodiments of the present disclosure will be described in detail with reference to the accompanying drawings. In the description of the exemplary embodiment of the present disclosure, a detailed description of known configurations or functions incorporated herein will be omitted when it is determined that the detailed description may make the subject matter of the present disclosure unclear. Further, the terms used in the description are defined considering the functions of the present disclosure and may vary depending on the intention or usual practice of a user or operator. Accordingly, the terms need to be defined based on details throughout this specification.

Hereinafter, exemplary embodiments of a product surface inspecting apparatus and method will be described in detail with reference to drawings. Hereinafter, the AI-based product surface inspecting apparatus and method may be abbreviated as a product surface inspecting apparatus and a product surface inspecting method, respectively.

Figure 1:
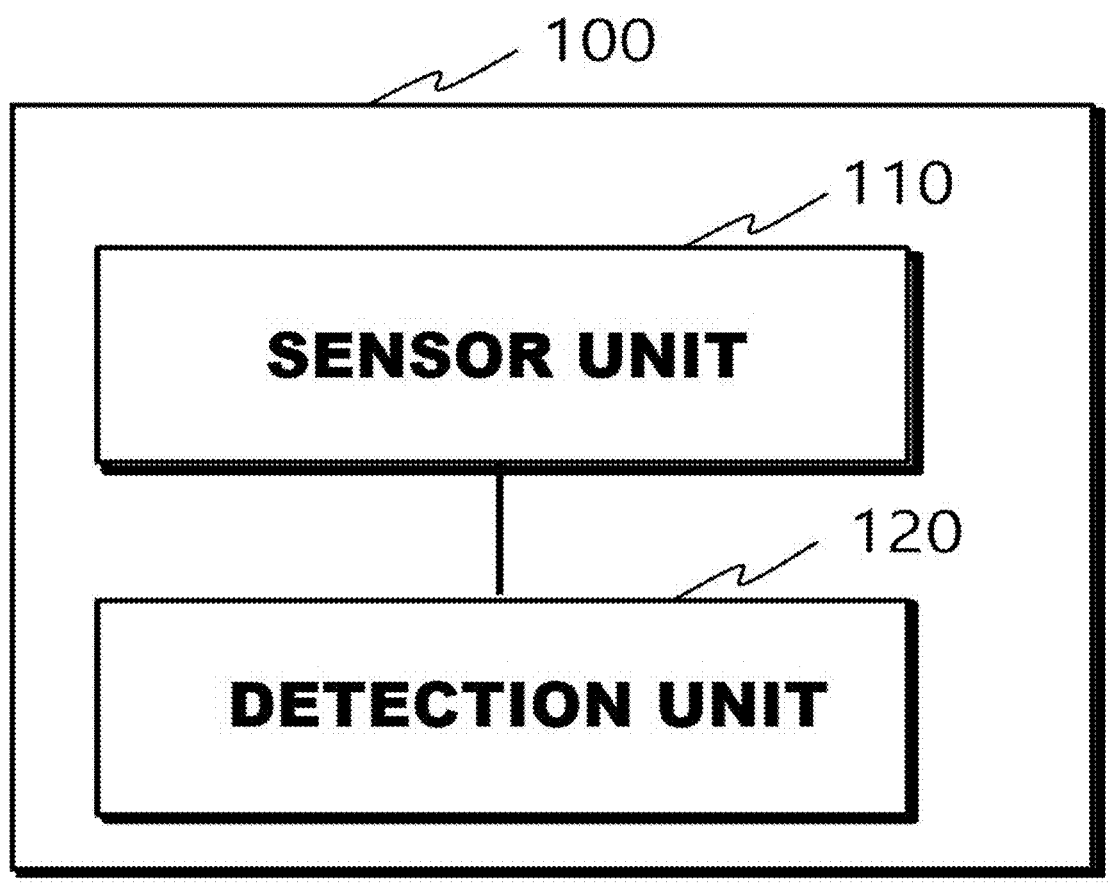
FIG. 1 is a configuration diagram of an AI-based product surface inspecting apparatus according to an exemplary embodiment.

FIG. 1 is a configuration diagram of a product surface inspecting apparatus according to an exemplary embodiment.

Referring to FIG. 1, the product surface inspecting apparatus 100 may include a sensor unit 110 and a detection unit 120.

According to an exemplary embodiment, the sensor unit 110 may photograph a product to generate image data. For example, the sensor unit 110 may include a camera sensor which photographs a product.

According to the exemplary embodiment, the sensor unit 110 may measure at least one of a color, a saturation, a brightness, a transparency, and a reflectance of the product. For example, the sensor unit 110 may include a separate sensor to measure at least one of a color, a saturation, a brightness, a transparency, and a reflectance or analyze at least one of the color, the saturation, the brightness, the transparency, and the reflectance by analyzing image data.

According to the exemplary embodiment, the detection unit 120 inputs image data to a convolutional neural network (CNN) trained to detect a defect on a product surface to detect a defect present on the product. According to an exemplary embodiment, the convolutional neural network may be configured by a plurality of convolution layers which performs a function of extracting a feature from a molded product.

According to the exemplary embodiment, the convolutional neural network may perform the learning by receiving a predetermined size of training image data for a first defect type to divide the training image data into grids having a predetermined size. For example, the training image data is configured by a three-channel image obtained by dividing an image for the same product with respect to the RGB and a size of the training data is 448×448, and a size of the grid is 7×7.

According to the exemplary embodiment, the convolutional neural network for product surface inspection may be trained by dividing layers to extract a feature of the defect based on the image data obtained by photographing the product. At this time, as the layer is deeper in the convolutional neural network, a width and a height of a defective part in the image data are reduced and a channel is increased.

According to the exemplary embodiment, the convolutional neural network may perform the training as many times as the number obtained by dividing the size of training image data by a size of the grid. For example, when it is assumed that a pixel size of image data including a defect is 448×448×3 (width×height×channel) and a pixel size of a defect image is 7×7, the convolutional neural network may learn different features for every channel 1024×4 times. According to an exemplary embodiment, the convolutional neural network may learn N defect types.

For example, the defect type of the product may be any one of a short shot, a black streak, a crack, a flash (burr), a flow mask, jetting, a sink mark, a silver streak, a warpage, a weld line, a cloudy surface, and delamination.

Figure 2:
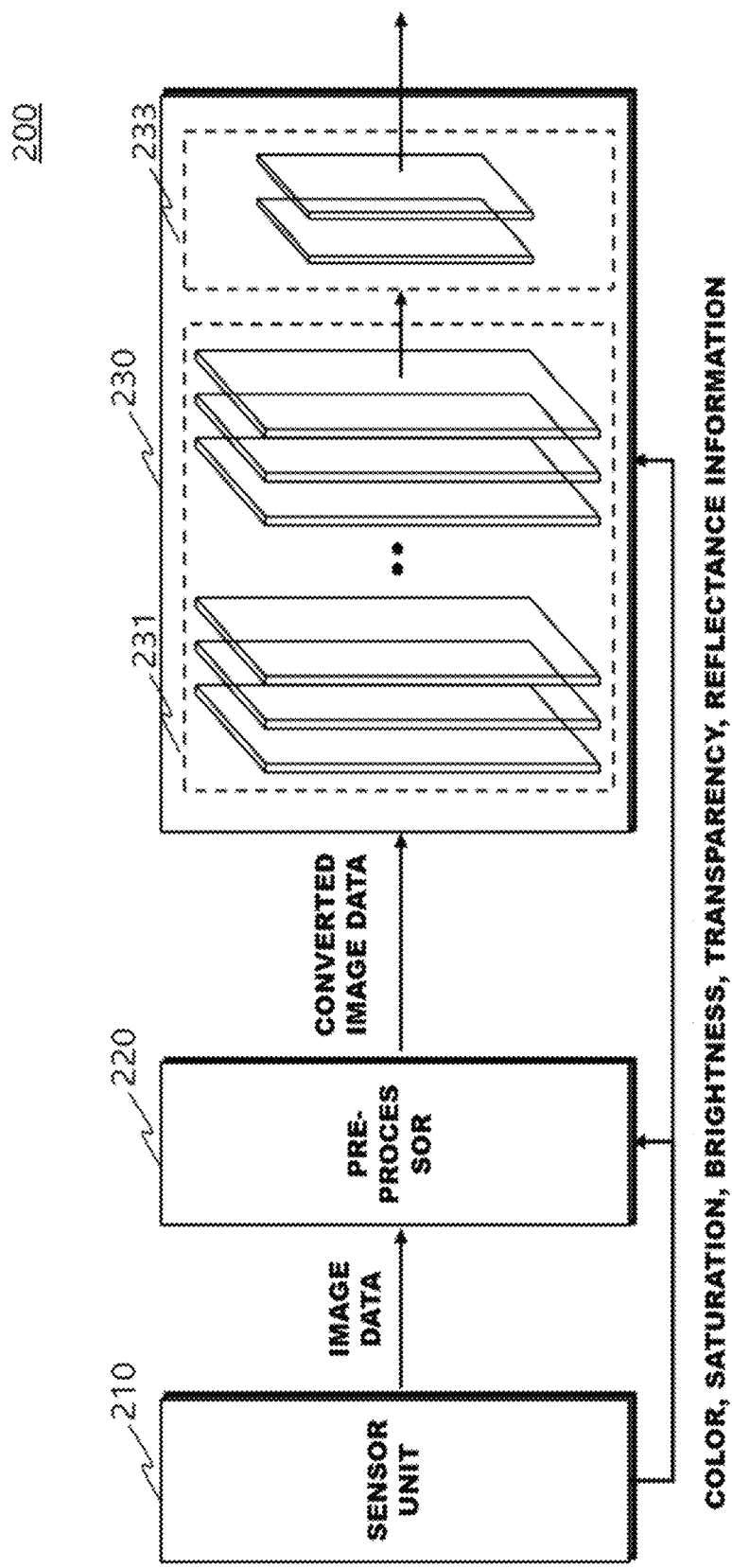
FIG. 2 is a configuration diagram of an AI-based product surface inspecting apparatus according to an exemplary embodiment.

Referring to FIG. 2, a detection unit 230 may include a plurality of convolution layers 231 and a plurality of fully connected layers.

According to the exemplary embodiment, the number of convolution layers of the convolutional neural network may be determined based on at least one of a color, a saturation, a brightness, a transparency, and a reflectance of the product. For example, depending on the color, the saturation, the brightness, the transparency, or the reflectance of the product, the difficulty of detecting a defect on the product surface may be worthwhile. For example, in the case of a dark color and opaque product, a silver streak on the product surface is easily detected and in the case of a bright color and transparent product, a silver streak on the product surface may be less noticeable. Accordingly, the number of convolution layers may be adjusted in consideration of a defect detection difficulty or a processing speed of the convolutional neural network.

According to the exemplary embodiment, the convolutional neural network may be trained using training data about a predetermined product and a product on which the actual detection is performed may have a different feature from a product of the training data. Accordingly, the configuration of the convolutional neural network may be adjusted by reflecting a feature of a product from which a defect is detected.

For example, the number of convolution layers of the convolutional neural network may be determined based on a similarity between at least one of the color, the saturation, the brightness, the transparency, and the reflectance of the product used as the training data of the convolutional neural network and at least one of a color, a saturation, a brightness, a transparency, and a reflectance of a product.

For example, when the feature of the product on which the detection is performed is similar to a product of the training data used to train the convolutional neural network, the convolutional neural network may detect a defect of the product with a relatively higher probability. In contrast, when the feature of the product on which the detection is performed is different from the product of the training data used to train the convolutional neural network, the convolutional neural network may detect a defect of the product with a relatively lower probability. Accordingly, the number of convolution layers which configures the convolutional neural network may be adjusted by comparing features of a product from which the defect is detected and the product of the training data used to train the convolutional neural network.

According to the exemplary embodiment, the number of convolution layers of the convolutional neural network may be increased in inverse proportion to the similarity. For example, if the similarity is high, the probability of detecting the defect may be relatively increased so that the number of convolution layers of the convolutional neural network is reduced to increase the processing efficiency. In contrast, when the similarity is low, the probability of detecting the defect is relatively lowered so that the number of convolution layers of the convolutional neural network is increased to improve a detection performance.

According to the exemplary embodiment, the product surface inspecting apparatus may further include a preprocessor which converts image data based on at least one of the color, the saturation, the brightness, the transparency, and the reflectance of the product to input the converted data to the detection unit.

Referring to FIG. 2, the preprocessor 220 may receive and convert image data generated in the sensor unit 210 to transmit the converted data to the detection unit 230. To this end, the preprocessor 220 may receive information about at least one of the color, the saturation, and the brightness of the product from the sensor unit 210. Alternatively, the preprocessor 220 may analyze the input image data to analyze at least one of the color, the saturation, and the brightness of the product.

According to the exemplary embodiment, the preprocessor 220 may perform auto cropping to extract a shape of the product from the image data to extract at least one feature of a brightness and a shadow of the product based on a shape of the automatically cropped product.

According to the exemplary embodiment, the preprocessor 220 may convert at least one of the color, the saturation, and the brightness of the image data with respect to at least one of the color, the saturation, and the brightness of the product used as the training data of the convolutional neural network.

For example, when the feature of the product from which the defect is detected and the feature of the product of the training data used to train the convolutional neural network are different, the performance of the detection unit 230 may be degraded. Accordingly, the preprocessor 220 may convert at least one of the color, the saturation, and the brightness of the product with respect to at least one of the color, the saturation, and the brightness of the product of the training data. For example, if it is assumed that if the brightness is high, the defect-detecting probability of the product is reduced, the preprocessor 220 may generate a converted image by lowering the brightness of the image data.

According to the exemplary embodiment, the preprocessor 220 may determine a frequency of an image sharpening filter based on a transparency of the product and convert the image data by applying the image sharpening filter to the image data.

For example, in the case of the transparent product, a stain on the product surface may not be easily distinguished from a normal part. Accordingly, in order to emphasize a delicate difference, a high frequency feature of image data needs to be highlighted. To this end, the preprocessor 220 may further highlight the high frequency performance of the image data using the sharpening filter. For example, the sharpening filter may be expressed as a high frequency pass filter or a high frequency emphasis filter.

According to an exemplary embodiment, the detection unit 120 detects a position of a defect, a size of the defect, and a type of defect present on the product. If a predetermined number or more of defects of the same position, same size, and same type consistently occur, it may be determined that the defect is not a defect.

According to the exemplary embodiment, the detection unit 120 may display a bounding box on the image data based on the position of the defect and the size of the defect present in the product and output image data displayed with the bounding box and the type of the defect. To this end, the product surface inspecting apparatus may further include an interface for outputting image data.

Figure 3:
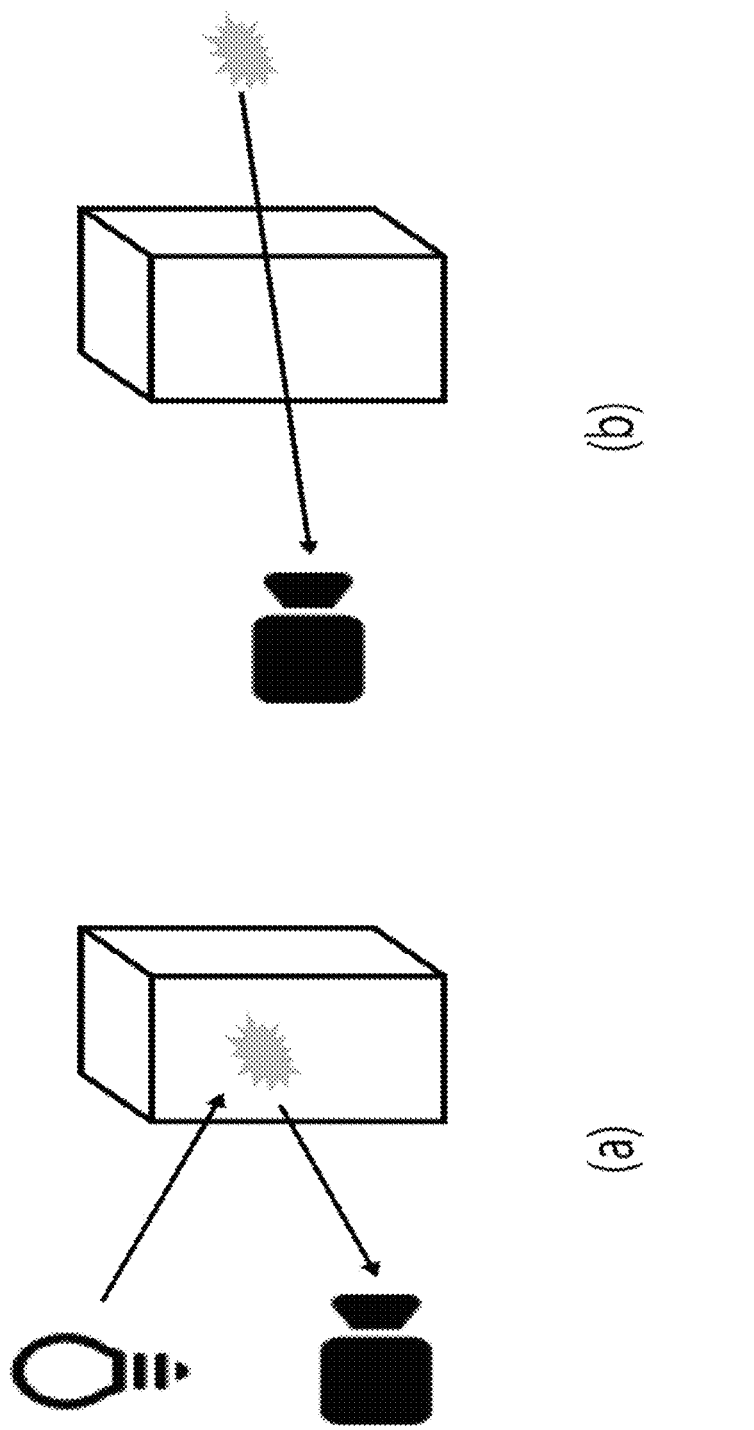
FIG. 3 is an exemplary view for explaining an operation of an AI-based product surface inspecting apparatus according to an exemplary embodiment.

Referring to FIG. 3A, when the sensor unit 110 generates image data of the product to detect the defect of the product, illumination light may be reflected on the product or other surrounding objects may be reflected. Specifically, in the case of a glossy product with a smooth surface, the influence according to the reflection may be significant.

For example, the detection unit 120 may erroneously detect a portion such as a stain due to the reflection as a defect. Accordingly, when the position of the defect, the size, and the type are consistently repeated, the detection unit 120 may determine that the defect is generated due to the external influence. In this case, the detection unit 120 may exclude the defect which is determined as a defect due to the external influence from the detection.

Figure 4:
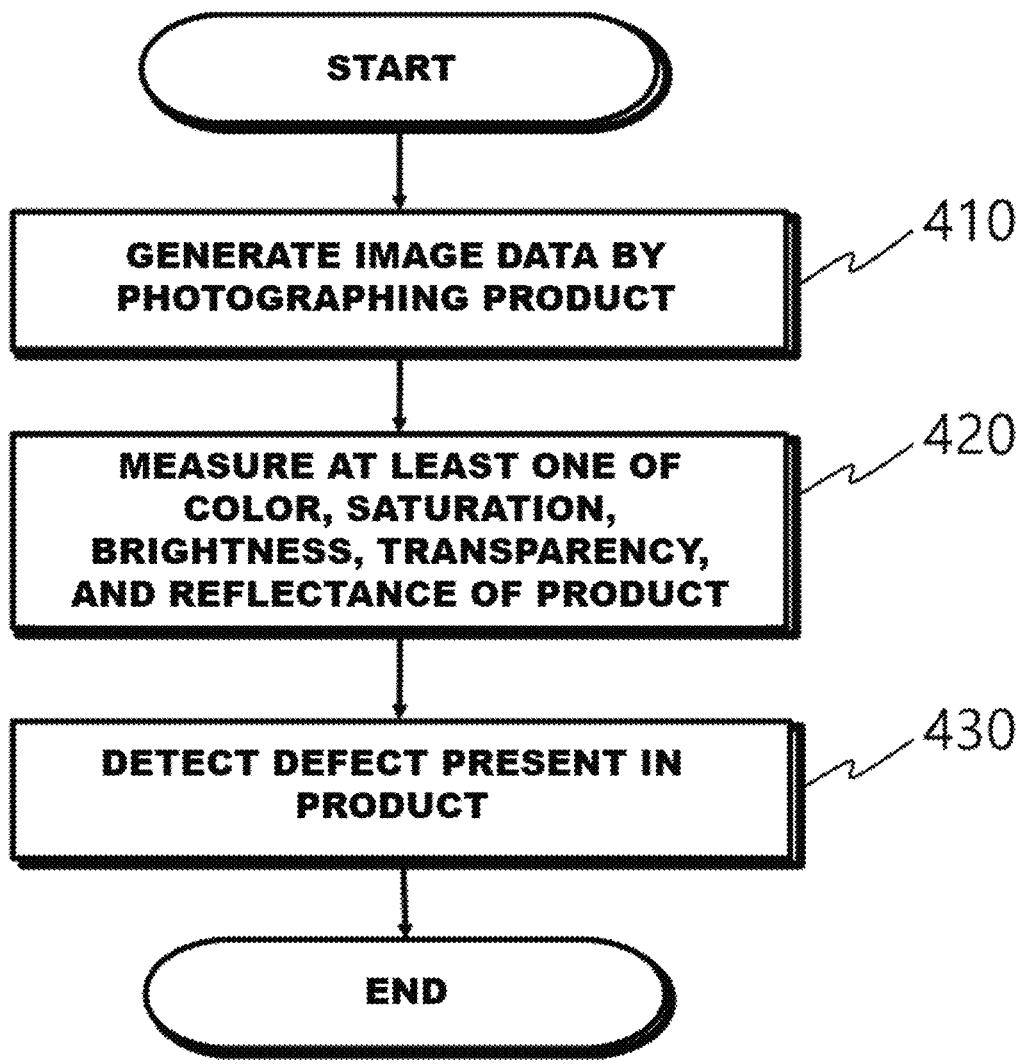
FIG. 4 is a flowchart illustrating an AI-based product surface inspecting method according to an exemplary embodiment.

Referring to FIG. 3B, when the sensor unit 110 generates image data of the product to detect the defect of the product, light which passes a transparent product or an image of another surrounding object may be photographed. Specifically, in the case of a product with a high transparency, the influence according to the transmission of a background may be significant. For example, the detection unit 120 may erroneously detect a portion such as an object on the background and a stain as a defect. Accordingly, when the position of the defect, the size, and the type are consistently repeated, the detection unit 120 may determine that the defect is generated due to the external influence. In this case, the detection unit 120 may exclude the defect which is determined as a defect due to the external influence from the detection. FIG. 4 is a flowchart illustrating a product surface inspecting method according to an exemplary embodiment.

According to an exemplary embodiment, the product surface inspecting apparatus may photograph a product to generate image data in step 410. For example, the product surface inspecting apparatus may include a camera sensor which photographs a product.

According to the exemplary embodiment, the product surface inspecting apparatus may measure at least one of a color, a saturation, a brightness, a transparency, and a reflectance of the product in step 420.

According to the exemplary embodiment, the product surface inspecting apparatus may measure at least one of a color, a saturation, a brightness, a transparency, and a reflectance of the product. For example, the product surface inspecting apparatus may include a separate sensor to measure at least one of the color, the saturation, the brightness, the transparency, and the reflectance or analyze at least one of the color, the saturation, the brightness, the transparency, and the reflectance by analyzing image data.

According to the exemplary embodiment, the product surface inspecting apparatus may input image data to a convolutional neural network (CNN) trained to detect a defect on a product surface to detect a defect present on the product in step 430.

According to an exemplary embodiment, the convolutional neural network is configured by a plurality of convolution layers which performs a function of extracting a feature from a molded product and a plurality of fully connected layers.

According to the exemplary embodiment, the number of convolution layers of the convolutional neural network may be determined based on at least one of a color, a saturation, a brightness, a transparency, and a reflectance of the product. For example, the number of convolution layers of the convolutional neural network may be determined based on a similarity between at least one of the color, the saturation, the brightness, the transparency, and the reflectance of the product used as the training data of the convolutional neural network and at least one of the color, the saturation, the brightness, the transparency, and the reflectance of the product.

According to the exemplary embodiment, the product surface inspecting apparatus may convert image data based on at least one of the color, the saturation, the brightness, the transparency, and the reflectance of the product. For example, the product surface inspecting apparatus may convert at least one of the color, the saturation, and the brightness of the image data with respect to at least one of the color, the saturation, and the brightness of the product used as the training data of the convolutional neural network. As another example, the product surface inspecting apparatus may determine a frequency of an image sharpening filter based on a transparency of the product and convert the image data by applying the image sharpening filter to the image data.

According to an exemplary embodiment, the product surface inspecting apparatus may detect a position of a defect, a size of the defect, and a type of defect on the product. If a predetermined number or more of defects of the same position, same size, and same type consistently occur, it may be determined that the defect is not a defect.

An aspect of the present disclosure may also be implemented as computer-readable codes written on a computer-readable recording medium. Codes and code segments which implement the program may be easily deducted by a computer programmer in the art. The computer readable recording medium may include all kinds of recording devices in which data, which are capable of being read by a computer system, are stored. Examples of the computer-readable recording media may include ROM, RAM, CD-ROM, magnetic tape, floppy disk, optical disk, and the like. the computer readable recording medium is distributed in computer systems connected through a network to be written and executed with a computer readable code in a distributed manner.

For now, the present disclosure has been described with reference to the exemplary embodiments. It is understood to those skilled in the art that the present disclosure may be implemented as a modified form without departing from an essential characteristic of the present disclosure. Accordingly, the scope of the present disclosure is not limited to the above-described embodiment, but should be construed to include various embodiments within the scope equivalent to the description of the claims.

The present disclosure is applicable to an industry of process automation.

The invention claimed is:

1. An AI-based product surface inspecting apparatus, comprising:
a sensor unit which photographs a product to generate image data and measures at least one of a color, a saturation, a brightness, a transparency, and a reflectance of the product; and
a detection unit which detects a defect on the product by inputting the image data to a convolutional neural network (CNN) trained to detect a defect on a product surface,
wherein a number of convolution layers of the convolutional neural network is determined based on a defect detection difficulty determined according to at least one of the color, the saturation, the brightness, the transparency, and the reflectance of the product and a defect type, and
wherein the detection unit detects a position of the defect, a size of the defect, and a type of the defect on the product and if a predetermined number or more of defects of the same position, same size, and same type occur in a predetermined consistency level, it is determined that the defect is not a defect.

2. The AI-based product surface inspecting apparatus according to claim 1, wherein the convolutional neural network performs a learning by receiving a predetermined size of training image data for a first defect type to divide the training image data into grids having a predetermined size.

3. The AI-based product surface inspecting apparatus according to claim 2, wherein the training image data is configured by a three-channel image obtained by dividing an image for the same product with respect to RGB and a size of the training data is 448×448, and a size of the grid is 7×7.

4. The AI-based product surface inspecting apparatus according to claim 2, wherein the convolutional neural network performs the learning as many as the number obtained by dividing a size of one training image data by a size of the grid.

5. The AI-based product surface inspecting apparatus according to claim 2, wherein the convolutional neural network learns N defect types.

6. The AI-based product surface inspecting apparatus according to claim 1, wherein the number of convolution layers of the convolutional neural network is determined further based on a similarity between at least one of the color, the saturation, the brightness, the transparency, and the reflectance of the product used as the training data of the convolutional neural network and at least one of the color, the saturation, the brightness, the transparency, and the reflectance of the product.

7. An AI-based product surface inspecting apparatus, comprising:
a sensor unit which photographs a product to generate image data and measures at least one of a color, a saturation, a brightness, a transparency, and a reflectance of the product; and
a detection unit which detects a defect on the product by inputting the image data to a convolutional neural network (CNN) trained to detect a defect on a product surface,
wherein a number of convolution layers of the convolutional neural network is determined based on a defect detection difficulty determined according to at least one of the color, the saturation, the brightness, the transparency, and the reflectance of the product and a defect type, and
wherein the number of convolution layers of the convolutional neural network is determined further based on a similarity between at least one of the color, the saturation, the brightness, the transparency, and the reflectance of the product used as the training data of the convolutional neural network and at least one of the color, the saturation, the brightness, the transparency, and the reflectance of the product, and wherein the number of convolution layers of the convolutional neural network is increased in inverse proportion to the similarity.

8. The AI-based product surface inspecting apparatus according to claim 1, further comprising:

a preprocessor which converts the image data based on at least one of the color, the saturation, the brightness, the transparency, and the reflectance of the product to input the converted data to the detection unit.

9. The AI-based product surface inspecting apparatus according to claim 8, wherein the preprocessor performs auto cropping to extract a shape of the product from the image data to extract at least one feature of a brightness and a shadow of the product based on a shape of the automatically cropped product.

10. The AI-based product surface inspecting apparatus according to claim 8, wherein the preprocessor converts at least one of the color, the saturation, and the brightness of the image data with respect to at least one of the color, the saturation, and the brightness of the product used as training data of the convolutional neural network.

11. The AI-based product surface inspecting apparatus according to claim 8 wherein the preprocessor determines a frequency of an image sharpening filter based on the transparency of the product and converts the image data by applying the image sharpening filter to the image data.

12. The AI-based product surface inspecting apparatus according to claim 1, wherein the detecting unit displays a bounding box on the image data based on the position of the defect and the size of the defect present on the product and outputs the image data displayed with the bounding box and the type of the defect.

13. An AI-based product surface inspecting method, comprising:

generating image data by photographing a product;

measuring at least one of a color, a saturation, a brightness, a transparency, and a reflectance of the product; and detecting a defect on the product by inputting the image data to a convolutional neural network trained to detect the defect on a product surface, wherein a number of convolution layers of the convolutional neural network is determined based on a defect detection difficulty determined according to at least one of a color, a saturation, a brightness, a transparency, and a reflectance of the product and a defect type, and wherein when detecting the defect on the product, a position of a defect, a size of the defect, and a type of the defect on the product are detected and if a predetermined number or more of defects of the same position, same size, and same type occur in a predetermined consistency level, it is determined that the defect is not a defect.

* * * * *